US010520419B2

(12) United States Patent
Hayden et al.

(10) Patent No.: US 10,520,419 B2
(45) Date of Patent: Dec. 31, 2019

(54) CARTRIDGE FOR A MAGNETIC FLOW CYTOMETER, A MAGNETIC FLOW CYTOMETER, AND METHOD FOR ANALYSING A SAMPLE WITH SUCH A CARTRIDGE

(71) Applicant: EarlyBio GmbH, Berlin (DE)

(72) Inventors: Oliver Hayden, Herzogenaurach (DE); Michael Johannes Helou, Regensburg (DE); Mathias Reisbeck, Regensburg (DE); Lukas Richter, Hirschaid (DE)

(73) Assignee: EarlyBio GmbH, Berlin (DE)

( * ) Notice: Subject to any disclaimer, the term of this patent is extended or adjusted under 35 U.S.C. 154(b) by 0 days.

(21) Appl. No.: 15/312,662

(22) PCT Filed: May 20, 2014

(86) PCT No.: PCT/EP2014/060333
§ 371 (c)(1),
(2) Date: Nov. 20, 2016

(87) PCT Pub. No.: WO2015/176744
PCT Pub. Date: Nov. 26, 2015

(65) Prior Publication Data
US 2017/0102313 A1    Apr. 13, 2017

(51) Int. Cl.
*B01L 3/00* (2006.01)
*G01N 15/10* (2006.01)
(Continued)

(52) U.S. Cl.
CPC .... *G01N 15/1031* (2013.01); *B01L 3/502776* (2013.01); *G01N 15/0656* (2013.01);
(Continued)

(58) Field of Classification Search
CPC ......... G01N 15/1031; G01N 33/54326; G01N 1/40; G01N 15/1056; G01N 33/585;
(Continued)

(56) References Cited

U.S. PATENT DOCUMENTS

2007/0017633 A1* 1/2007 Tonkovich ............ B01F 5/0611
156/300
2007/0264675 A1* 11/2007 Toner ................ B01L 3/502746
435/7.23
(Continued)

FOREIGN PATENT DOCUMENTS

WO    WO 2008048616 A2    4/2008
WO    WO 2010124001 A1    10/2010

OTHER PUBLICATIONS

PCT International Search Report and Written Opinion of the International Searching Authority dated Aug. 7, 2014, for corresponding PCT/EP2014/060333.

*Primary Examiner* — Dean Kwak
(74) *Attorney, Agent, or Firm* — McCoy Russell LLP (57) ABSTRACT

The invention relates to a cartridge (1) for a magnetic flow cytometer, mainly extending in a x-y-plane, with an inlet (2) for injecting a sample (15) into the cartridge (1), a blister (3) for a buffer solution (21) with magnetic markers to mark pregiven particles (16, 16') of the sample (15), an outlet, and a fluid channel (9), the fluid channel (9) comprising a first part that connects the inlet (2) with the blister (3) and a second part that connects the first part with the outlet, wherein the second part of the fluid channel (9) comprises an enrichment zone (5) with mechanical guiding structures to focus marked particles (16, 16') of the sample (15) in a predetermined subsection of the fluid channel (9) and a measuring zone (6) between the enrichment zone (5) and the outlet, the measuring zone (6) comprising a magnetic field sensor (14) in the predetermined subsection of the fluid
(Continued)

channel (9) in order to provide simplified and accelerated means for measuring particles, in particular concentrations of particles, of a sample.

13 Claims, 5 Drawing Sheets

(51) Int. Cl.
  *G01N 33/543* (2006.01)
  *G01N 15/06* (2006.01)
  *G01N 15/00* (2006.01)
(52) U.S. Cl.
  CPC ... *G01N 15/1056* (2013.01); *G01N 33/54326* (2013.01); *B01L 2200/0668* (2013.01); *B01L 2300/087* (2013.01); *B01L 2300/0816* (2013.01); *B01L 2300/0867* (2013.01); *B01L 2300/0883* (2013.01); *B01L 2400/043* (2013.01); *B01L 2400/0481* (2013.01); *B01L 2400/086* (2013.01); *G01N 2015/0053* (2013.01); *G01N 2015/0065* (2013.01); *G01N 2015/0092* (2013.01); *G01N 2015/1006* (2013.01); *G01N 2015/1062* (2013.01)
(58) Field of Classification Search
  CPC ......... G01N 2015/1006; G01N 27/745; G01N 15/1404; G01N 35/0098; G01N 15/0656; G01N 2015/0065; G01N 2015/1062; G01N 2035/00564; G01N 27/72; G01N 33/54333; G01N 33/54366; G01N 2015/0053; G01N 2015/1422; G01N 2291/0256; G01N 2291/02809; G01N 29/036; G01N 29/2412; G01N 33/5094; G01N 33/54373; G01N 33/587; G01N 33/80; G01N 33/86; G01N 2400/043; B01L 2400/043; B01L 3/502761; B01L 2300/0816; B01L 2200/0652; B01L 2400/086; B01L 3/502776; B01L 2300/0877; B01L 2200/0668; B01L 3/502746; B01L 2300/0627; B01L 2300/0867; B01L 2300/087; B01L 2300/089; B01L 2400/0481; B01L 3/5027; B03C 1/288; B03C 2201/26; B03C 2201/18; B03C 1/01; B03C 2201/24; B03C 1/0332; B03C 1/0335; B03C 1/034; B03C 1/286; B03C 1/02; B03C 2201/20
  USPC .............................. 422/73, 501–504; 436/10
  See application file for complete search history.

(56) References Cited

U.S. PATENT DOCUMENTS

| | | | |
|---|---|---|---|
| 2009/0053799 A1* | 2/2009 | Chang-Yen | B03C 1/01 435/287.2 |
| 2010/0022680 A1* | 1/2010 | Karnik | A61K 47/6937 523/105 |
| 2011/0117577 A1 | 5/2011 | Reboud et al. | |
| 2012/0122731 A1* | 5/2012 | Soh | B01L 3/502761 506/12 |
| 2012/0187938 A1 | 7/2012 | Bar et al. | |
| 2013/0256197 A1* | 10/2013 | Katsumoto | B03C 5/026 209/127.1 |
| 2013/0337497 A1 | 12/2013 | Hayden et al. | |
| 2014/0295460 A1* | 10/2014 | Weissleder | G01N 27/745 435/7.23 |

* cited by examiner

CARTRIDGE FOR A MAGNETIC FLOW CYTOMETER, A MAGNETIC FLOW CYTOMETER, AND METHOD FOR ANALYSING A SAMPLE WITH SUCH A CARTRIDGE

The invention relates to a cartridge for a magnetic flow cytometer, mainly extending in a x-y-plane, with an inlet for injecting a sample into the cartridge, a blister for a buffer solution with magnetic markers to mark pregiven particles of the sample, an outlet, and a fluid channel, the fluid channel comprising a first part that connects the inlet with the blister and a second part that connects the first part with the outlet. It furthermore relates to a magnetic flow cytometer with such a cartridge and to measuring particles of a sample by a magnetic flow cytometer using such a cartridge.

Measuring particles or samples with particles, in particular blood or the alike, by means of a magnetic flow cytometer usually involves a series of steps to be taken. The particles, for example cells, have to be marked and enriched by repeated addition and removal of buffer solutions. If a marker is added to a sample in a buffer solution, the sample usually is diluted or thinned out by the buffer solution, and eventually chemical substances of the buffer solution may get in contact with the sample, hence changing its characteristics.

It is an object of the present invention to provide simplified and accelerated means for measuring particles, in particular concentrations of particles, of a sample.

This object is solved by a cartridge having the features of patent claim 1 and a method having the features of patent claim 11.

Further advantages and embodiments are set out according to the dependent claims, the detailed description and the figures.

An inventive cartridge for a magnetic flow cytometer mainly extends in an x-y-plane perpendicular to a z direction and comprises an inlet for injecting a sample into the cartridge, a blister for a buffer solution with magnetic markers to mark pregiven particles of the sample, an outlet, and a fluid channel. The inlet may be designed to connect a syringe to the cartridge. The fluid channel comprises a first part that connects the inlet with the blister and a second part that connects the first part with the outlet. The outlet may be connected to a waste container. The blister may be a blister, a pouch, or another form of container suited for use in a cartridge. It may already contain the buffer solution with magnetic markers. The magnetic markers may be immunomagnetic markers that mark only specific, predetermined particles of the sample. In particular, these specific particles may be leukocytes and/or platelets and/or lymphocytes and/or monocytes, in particular monocytes expressing HL-DR, and/or eosinophil granulocytes and/or basophil granulocytes and/or neutrophil granulocytes, in particular neutrophil granulocytes expressing CD 64, and/or tumour cells of a biological sample.

In order to provide for a fast and simple measuring of the pregiven particles of the sample, the second part of the fluid channel comprises an enrichment zone with mechanical guiding structures to focus the marked pregiven particles in a predetermined subsection of the fluid channel and a measuring zone between the enrichment zone and the outlet. The measuring zone comprises a magnetic field sensor in the predetermined subsection of the fluid channel. The magnetic field sensor may be a sensor based on the giant magnetoresistive (GMR) effect or on the tunnel magnetoresistive (TMR) effect. It also may be a Hall sensor or a superconducting quantum interference device (SQUID). The predetermined subsection of the fluid channel may be a subsection of a cross section perpendicular to a flow direction of the sample in the fluid channel. In particular, the predetermined subsection of the fluid channel may be that volume of the fluid channel in which, provided the mechanical guiding structures would not exist, any particle following the flow of the sample through the fluid channel would pass the magnetic field sensor in a distance as small as possible so that the particle could be measured by the magnetic field sensor in an optimal way.

This gives the advantage of measuring particles, in particular the concentration of particles, in several orders of magnitude without the need to dilute or enrich the sample containing the particles with additional, time-consuming and expensive steps. Furthermore, this high dynamic range is achieved independently of the capacity of the magnetic sensor. So, identical magnetic sensors may be used in cartridges meant for different types of samples. Furthermore, a corruption of the measurement due to coincidence of particles in close proximity of the sensor due to variations in the concentration of the particles in the sample can be avoided. This is especially useful when the sample is whole blood. With the proposed cartridge, measuring a sample of whole blood is even possible when the whole blood is not stabilized. This allows to reproduce in vivo conditions when running diagnostics with a flow cytometer, which is important when it comes to analysing the function of cell e.g. for cellular haemostasis, sepsis or trauma. The proposed cartridge also allows for an integrated workflow for patient's side diagnostics of cellular functions, e.g. in an emergency room of a hospital. Typically only three minutes are required for testing for a cellular haemostasis and about ten minutes are required for haematology tests with the proposed cartridge.

Testing for cellular haemostasis may for instance include measuring concentration, function, i.e. the ability to be activated, and micro aggregation of platelets. The haematology test may include measuring the expression of CD 64 on neutrophil granulocytes and/or the expression of HL-DR on monocytes.

Furthermore, the cartridge allows for time critical patient's side measurements of cell concentrations, e.g. counting platelets or white blood cells in liquor down to e.g. four white blood cells per microliter, detecting tumour cells in urine, or alike. Furthermore, the cartridge allows measuring the properties and characteristics of particles like platelets that have been exposed to a defined shear rate on a boundary surface of a substrate, i.e. on a surface of the fluid channel. Finally, the proposed cartridge allows sorting particles, in particular cells, by number and function within the scope of point-of-care-testing (POCT).

According to a preferred embodiment, the cartridge has a fluid chamber which is a part of the fluid channel, in particular a fluid chamber in the first part of the fluid channel, for mixing the sample with the markers. The fluid chamber has physical dimensions, in particular a diameter, larger than those of the fluid channel in the x- and/or y- and/or z-direction, in particular many times larger. There also may be a mixing device in the fluid chamber. This gives the advantage that in the fluid chamber the markers can be fixed by means of a magnetic field while the rest of the buffer solution can be flushed away. Then, the markers can be mixed with the sample in a larger volume than that of the fluid channel alone. Thus, an especially large ratio of the pregiven particles of the sample may be marked. This is particularly useful if the particles that are to be marked by the magnetic markers have a low concentration in the sample. Since a relatively large proportion of the particles can be marked, sufficient statistics for the measuring can be achieved also in the case of low concentrations of the particles. Also, the fluid chamber allows to achieve a defined dilution of the sample for the process of marking the pregiven particles and still execute the process of measuring the marked particles while they are surrounded by an undiluted or unthinned sample.

According to another embodiment, the mechanical guiding structures comprise the fluid channel decreasing in its extension in the z-direction in the enrichment zone as the fluid channel gets closer to the measuring zone. In particular, this decreasing can be realized stepwise, dividing the fluid channel in different sections that have a different height, i.e. a different extension in the z-direction. This gives the advantage that the particles are focussed close to a surface of the fluid channel perpendicular to the z-direction.

Furthermore, if the diameter of the fluid channel in a direction perpendicular to the z-direction and the direction of flow does not compensate the decrease of height, the sample will flow through the different sections of the fluid channel at different speed. This allows exerting a defined shear rate or shear stress on the particles for a pregiven flow rate and/or pre given flow speed through the fluid channel. This is advantageous for activating platelets, for example.

In yet another embodiment, the mechanical guiding structures comprise a multitude of elevations, in particular walls, extending on a surface of the fluid channel in the x-y-plane. In particular the elevations have an extension in the z-direction of more than half of a diameter of the particles that are to be marked. These elevations may be straight or at least comprise straight parts. This gives the advantage to guide the marked particles, especially when they are pulled towards the said surface of the fluid channel by the magnetic field, towards a specific direction or area, in particular the predetermined subsection of the fluid channel. An extension in the z-direction of more than half of the diameter of the particles to be marked is advantageous since then the elevations or walls can be overcome not easily by the particles. Hence, effective guiding is achieved.

The elevations may be pointing, from a perspective of a flow through the fluid channel towards the outlet, either towards the predetermined subsection of the fluid channel to guide particles to the predetermined subsections or be pointing away from the predetermined subsection in order to guide away from the magnetic field sensor particles that are close to but not within the predetermined area. Also combinations of elevations pointing towards and away from the predetermined subsections can be realized. At least a part of the elevations pointing towards the predetermined subsection may or all of them may also form structures with the shape of a "v", with the point of the "v" lying inside the predetermined subsection and pointing in the flow direction. So, with respect to the flow direction through the fluid channel towards the outlet, the elevations are approaching the predetermined subsection when they point towards it and veering away from the predetermined subsection if they are pointing away from it. This gives the advantage that the concentration of the particles in the measurement zone can be adjusted. Furthermore, a coincident, simultaneous flow of several particles next to each other passing by the magnetic sensor and thus corrupting the results of the magnetic sensor can be avoided.

According to another embodiment, the predetermined subsection of the fluid channel can be the middle or centre or central part of the fluid channel, i.e. the middle of a flow through the fluid channel in the x-y-plane on a surface of the fluid channel. This gives the advantage that a homogeneous magnetic field, which is advantageous for most magnetic field sensors, can be realized in the predetermined subsection very easily. Also, the concentration and the focus of the particles in the predetermined subsection can be controlled easily.

In another advantageous embodiment, the fluid channel meanders in the enrichment zone in order to lengthen a path in which the particles are guided by the mechanical guiding structures. This gives the advantage that, due to the lengthened path, particles can be focussed very precisely while still allowing the cartridge to have compact dimensions and using a relatively small, compact magnetic field for guiding the particles in the enrichment zone.

In a further embodiment, the measuring zone comprises a well that, from a perspective of the flow through the fluid channel towards the outlet, is located behind the magnetic field sensor. This well may be a pit or a cavity. Thus, the well acts as a trap for particles that have passed the magnetic field sensor. The well or the cartridge close to the well may comprise an auxiliary outlet. This gives the advantage that the measured particles can be collected in a first step and then be extracted from the cartridge easily via the auxiliary outlet in a second step to be used in further applications.

In yet another embodiment, the fluid channel, in particular the fluid channel in the measurement zone, has a broadness between 250 and 2500 micrometer and a height between 50 and 600 micrometers, or a cross sectional area with a size corresponding to a rectangle with the above broadness and height. Broadness and height are calculated perpendicular to a flow direction through the fluid channel, height in z-direction and broadness in the x-y-plane. This gives the advantage that a predefined shear rate or shear stress can be realized in the sample when it flows through the fluid channel where the shear rates are similar to the shear rates that appear in in-vivo conditions.

The invention also comprises a magnetic flow cytometer with the cartridge according to any of the described embodiments, with a magnet, in particular a permanent magnet, extending in an x-y-plane beneath the enrichment zone and/or the measuring zone, where the magnetic field sensor is located above a centre of the magnet in the x-y-plane. In particular, the area above the center of the magnet is characterized by a homogeneous magnetic field with components mainly in the z-direction. This gives the advantage that the magnetic field sensor can be used to measure magnetically marked particles by a change of the magnetic field. Furthermore, marked particles can be pulled towards a surface of the fluid channel. Consequently, when the marked particles are flowing through the fluid channel, they may actually be rolling on the surface they are pulled to.

In particular the marked particles can be pulled towards the surface with the mechanical guiding structures and hence be focussed for proper measuring by the magnetic field sensor when flowing or rolling through the fluid channel.

If the magnetic flow cytometer is designed to be used with a cartridge comprising the above-described fluid chamber, an additional magnet may be used to fix the markers in the fluid chamber and/or mix them with the sample. The additional magnet may be a moveable magnet or an electric magnet in order to release the markers and hence let the then-marked particles flow through the fluid channel towards the measuring zone at some point.

The invention also comprises a method for measuring particles of a sample by a magnetic flow cytometer using a cartridge for the magnetic flow cytometer that comprises an inlet for injecting a sample into the cartridge, a blister with a buffer solution with magnetic markers to mark predetermined particles of the sample, an outlet, and a fluid channel that comprises a first part that connects the inlet with the blister and a second part that connects the first part with the outlet. The method comprises the steps of activating the blister so that the buffer solution with the magnetic markers flows into the fluid channel followed by a fixing of the magnetic markers in a predetermined position of the fluid channel by means of a magnetic field. This is followed by injecting the sample into the fluid channel so that the buffer solution in the fluid channel is pushed towards the outlet, and the sample flows through the fluid channel so that at least some of the predetermined particles of the sample get marked by the magnetic markers in the predetermined position. The next step is focussing the marked particles in a predetermined subsection of the fluid channel by means of mechanical guiding structures in an enrichment zone in the second part of the fluid channel when they are flowing through the fluid channel or, preferably, rolling on a surface of the fluid channel through the fluid channel. This focussing is at least supported, in particular even made possible, by the influence of a magnetic field. Finally, the method comprises measuring the marked particles by means of a magnetic field sensor in the predetermined subsection of the fluid channel, the magnetic field sensor being located in a measuring zone between the enrichment zone and the outlet. The method may also comprise connecting a container with the sample to the inlet prior to activating the blister. In addition to the advantages of the cartridge and the magnetic flow cytometer that have been described above, this method gives the advantage that the magnetic markers are cleaned from the buffer solution when they are fixed in the predetermined position by the sample that washes away the buffer solution that originally surrounds the magnetic markers. Thus, the sample is not diluted or thinned by the buffer solution when it finally includes the marked particles.

In a preferred embodiment of the invention, the magnetic markers are fixed in a fluid chamber and are mixed with the sample in the fluid chamber after injecting the sample into the cartridge. This gives the advantage that a high portion or even all of the predetermined particles of the sample can be marked even if their concentration in the sample is very low. A concentration can be regarded as low when, for example, there are available less than 10.000 particles per microliter of the sample. Hence, this embodiment is especially useful when it comes to measure leukocytes in a liquor or tumour cells in urine or generally in the field of haematology.

According to an alternative embodiment, the magnetic markers are fixed on a surface of the fluid channel in the enrichment zone, in particular by means of the magnetic field used for measuring the particles in combination with the magnetic field sensor. This gives the advantage that only a small portion of the predefined particles in the sample are marked, since the markers are fixed on a surface of the fluid channel and only those of the predetermined particles that pass very close to that surface are marked by the markers. This is especially useful when there is a high concentration of the predetermined particles in the sample, for example more than 1000 particles per microliter. This is especially useful in the field of haemostasis, where the predetermined particles, in particular platelets, may reach concentrations up to one million particles per microliter.

According to another embodiment, a flow speed of the sample through the fluid channel is adjusted to a pregiven value, so that a pregiven shear rate or shear stress of the particles of the sample is achieved. Here, the shear rate depends on both the particles and the geometry of the fluid channel of the cartridge at hand. In particular, the flow speed through the measuring zone of the fluid channel may be adjusted. For instance, a combination of high and low flow rate through the fluid channel, in particular with a short pause before or inbetween, may result in a shearing of only those particles within a boundary layer of the sample with respect to the fluid channel. This gives the advantage that in-vivo conditions for the predetermined particles, for example platelets, can be simulated. As these conditions can have an influence on the activity of particles, namely platelets, this has an impact on the functional analysis of the particles.

In an advantageous embodiment, the sample that is used for the method is a biological sample. It may be a sample of blood, in particular whole blood, or liquor of lymph or urine or gastric lavage. This is advantageous for patient side diagnostics.

All attributes of the cartridge and/or the flow cytometer and the corresponding advantages are also applicable to the described method and vice versa.

By considering the following detailed description of exemplary embodiments in conjunction with the accompanying drawings, the teachings of the present invention can be readily understood, and at least some additional specific details will appear. Herein

Identical or corresponding elements are marked in the figures with the same reference signs.

Figure 1:
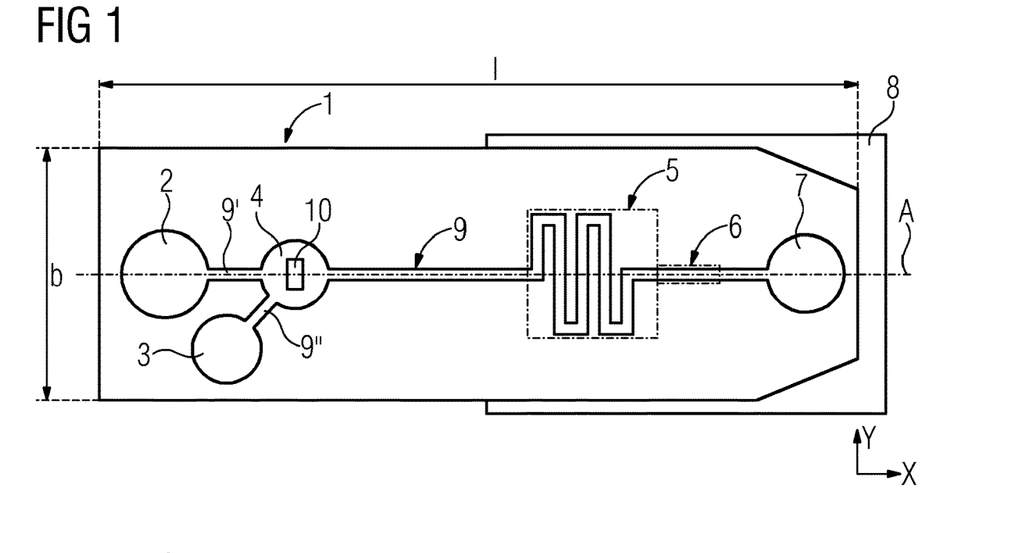
FIG. 1 shows a schematic illustration of an exemplary embodiment of a cartridge for a magnetic flow cytometer in an x-y-plane.

FIG. 1 shows a schematic illustration of an exemplary embodiment of a cartridge for a magnetic flow cytometer. The cartridge 1 extends mainly in an x-y-plane. It may be of rectangular or mainly rectangular shape, in the present example with the length 1 in x-direction of 75 mm and a broadness b in the y-direction of 25 mm, for example. It also extends in a z-direction perpendicular to x- and y-direction, but to a significantly lower extent. The present embodiment comprises an inlet 2, a blister 3 and a fluid chamber 4 in the left side, i.e. the side of the cartridge 1 extending into negative x-direction, and an enrichment zone 5 as well as a measuring zone 6 and, in the present example, a waste container 7 in the right hand side of cartridge 1. When the cartridge 1 is used in a magnetic flow cytometer, its part on the right hand side is exposed to an influence of a magnet 8, that is also depicted in the present illustration. Typically, the magnet 8 of a magnetic flow cytometer is a permanent magnet or an electromagnet. In the present illustration the magnet 8 is located beneath, i.e. in negative z-direction, of the right side of the cartridge 1 so that the enrichment zone 5 and the measuring zone 6 are located above the magnet 8.

In the left side of the cartridge 1, the inlet 2 and the fluid chamber 4 are connected with each other directly via a fluid channel connection 9'. Similarly, the blister 3 and the fluid chamber 4 are connected with each other directly via a fluid channel connection 9". These two fluid channel connections 9', 9" and the fluid chamber 4 form the first part of the fluid channel 9 in the present example. Here, the fluid chamber 4 also features a mixing device 10 that can be used, for example by being set in motion, to mix a buffer solution with magnetic markers with a sample comprising predetermined particles the markers are meant to mark. From the fluid chamber 4, the fluid channel 9 extends in positive x-direction towards the right side of the cartridge 1 in this embodiment. After reaching an area of the cartridge 1 above the magnet 8, in the present example, the fluid channel 9 starts to meander in an enrichment zone 5. So, within the enrichment zone 5, the fluid channel makes several turns and leads or runs not only in the x-direction but also in positive and negative y-direction. By running in positive and negative y-direction the fluid channel is lengthened in the enrichment zone 5. This allows mechanical guiding structures that are not shown in the present figure to better focus marked particles of a sample flowing through the fluid channel 9. Following the enrichment zone 5, the fluid channel 9 has a measuring zone 6, in which a magnetic field sensor 14 (FIG. 4-9) that is not depicted in the present figure is located. In this example, the fluid channel 9 then leads to a waste container 7.

Figure 2:
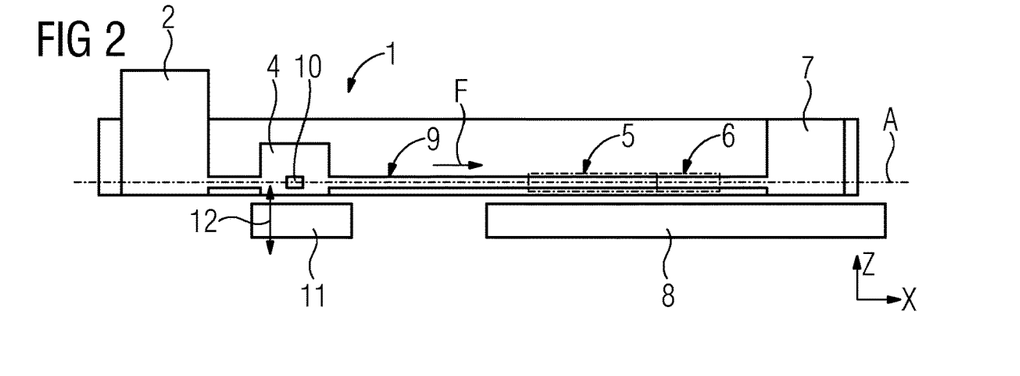
FIG. 2 shows a schematic cross section of the exemplary embodiment of a cartridge of FIG. 1 in an x-z-plane.

FIG. 2 shows a schematic cross section of the cartridge of FIG. 1 along an axis A in an x-z-plane. It becomes apparent that the fluid chamber 4 is larger than the fluid channel 9, i.e. in the present example it extends in the z-direction much more than the fluid channel 9. This allows the mixing device 10 to mix a relatively large volume of the sample with the markers. So, large ratios of the particles that are to be marked by the marker are actually marked. In order to fix or hold the magnetic markers and hence, once they are marked, the predetermined particles of the sample within the fluid chamber 4, there is an additional magnet 11 near the fluid chamber 4 that can be activated and deactivated. In the present example, the additional magnet 11 is simply moved towards the cartridge 1 if the markers are to be fixed in the fluid chamber 4 and moved away from the cartridge 1 if the marked particles are to flow through the fluid channel 9. This movement is depicted by the arrow 12. Alternatively, the additional magnet 11 can be an electromagnet that is switched on and off as needed.

The present embodiment is particularly useful if the particles that are to be marked by the magnetic marker have a relatively low concentration in the sample. For example, this is the case when there are less than 5.000 particles per microliter of the sample. If the sample is a blood sample, this may for instance be the case for white blood cells. In this case, the magnetic markers of the buffer solution are fixed in the fluid chamber 4 by the additional magnet 11 when the sample that is injected to the cartridge 1 by the inlet 2 pushes away the buffer solution from the fluid chamber 4 without the markers and replaces it. As there are not many of the predetermined particles that are bound to be marked in the sample in such a setting, using the mixing device 10 to mix the magnetic markers and the sample increases the probability of marking the predefined particles of the sample. Hence using the mixing device 10 improves a measurement of the sample, i.e. of the particles, in the measuring zone 6. Alternatively, the sample may not push the buffer solution away completely, so that the sample may be thinned down in a predefined way by the remains of the buffer solution in the fluid chamber 4.

Figure 3:
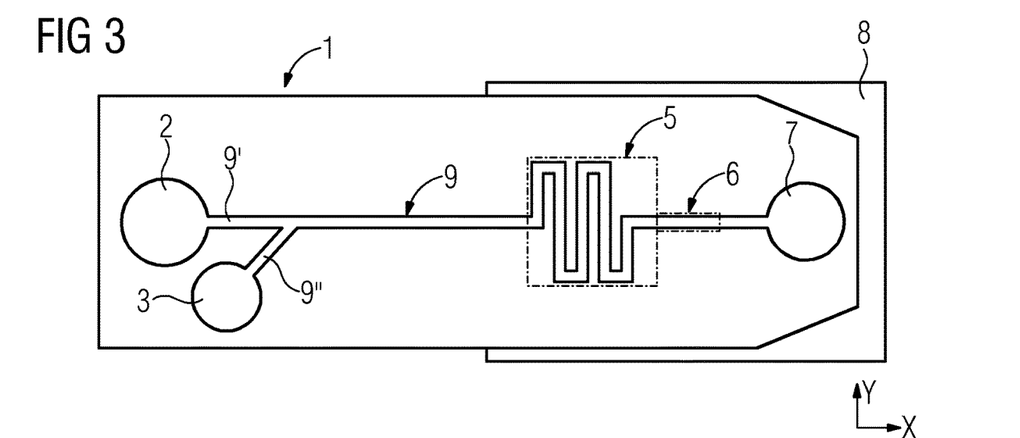
FIG. 3 shows a schematic illustration of an alternative embodiment of the cartridge for a magnetic flow cytometer in an x-y-plane.

FIG. 3 shows a schematic illustration of an alternative embodiment of the cartridge 1 in an x-y-plane. In contrast to the embodiment depicted in the FIGS. 1 and 2, the shown embodiment lacks the fluid chamber 4. Thus, the fluid channel connections 9', 9" feed or lead into another directly in the present example. In this example, the inlet 2 of the cartridge 1 is connected directly to the enrichment zone 5 by the fluid channel 9. The fluid channel connection 9" of the blister 3 leads directly into the fluid channel 9. Such a setup is especially useful if the concentration of the particles that are to be marked is specifically high in the sample. For example, this is the case if the concentration of the predetermined particles that are to be marked is more than 20.000 particles per microliter.

When the blister 3 with the buffer solution and the magnetic markers in the buffer solution is activated, the buffer solution and the magnetic markers flow through the fluid channel connection 9", the fluid channel 9, the enrichment zone 5 and the measuring zone 6 into the waste container 7 in the present setup. At least a fraction of the markers, though, is fixed in a predetermined position of the fluid channel 9, in this case in the enrichment zone 5. When the sample with the predefined particles that are to be marked is injected in the inlet 2 of the cartridge 1, there is no specific mixing of markers and particles with the mixing device 10 or alike. Instead, only some particles get in direct physical contact with the markers and are then marked. As the markers are magnetic and exposed to the magnetic field of the magnet 8, e.g. in the right hand side of the cartridge 1, the magnetic markers are fixed at the bottom of the fluid channel 9, i.e. the surface of the fluid channel 9 that is closest to the magnet 8, in the present example. In this case, the design of the cartridge 1 takes advantage of the laminar flow properties of the sample flowing through the fluid channel 9, in particular the enrichment zone 5, where mainly a first layer of particles directly above the bottom of the fluid channel 9 gets in touch with the markers. Consequently, only a defined, small ratio of the particles is marked homogenously and can hence be measured in the measuring zone 6. In the case of a large concentration of the predetermined particles, it is important to mark only a small portion of them in order to avoid coincidences of several marked particles flowing close by the magnet field sensor 14 (FIG. 4-9). Furthermore, a low amount of markers or antibodies can be used to mark the particles in spite of their high concentration. Such high concentrations are e.g. important when measuring platelets in a blood sample.

Figure 4:
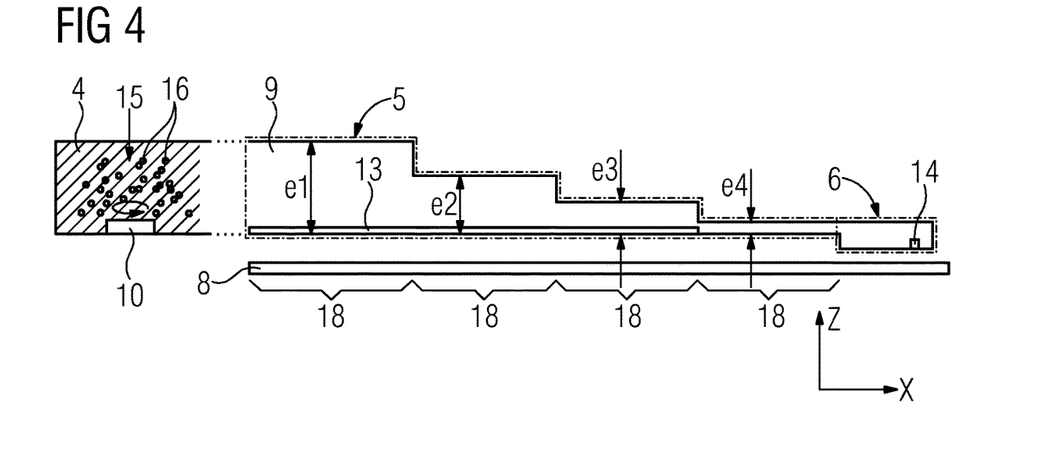
FIG. 4 shows a schematic cross section of an exemplary embodiment of a fluid channel with sample and particles in a fluid chamber.

FIG. 4 shows a schematic cross section through an exemplary linear fluid channel 9 in an x-z-plane with the sample 15 including the particles 16 in the fluid chamber 4. The fluid channel 9, in the present embodiment, extents straight in a line in the x-direction from the fluid chamber 4 via an intermediate section of arbitrary length to the enrichment zone 5, and from there to the measuring zone 6. In this illustration, the mixing device 10 is shown in action, so the particles 16 are currently being mixed with markers that are not depicted here. In the enrichment zone 5, the fluid channel 9 features an extension $e_1$, $e_2$, $e_3$, $e_4$ in the z-direction that decreases stepwise. Namely, in the present example, the extension $e_1$, $e_2$, $e_3$, $e_4$ decreases from a first extension $e_1$ by about 25% to a second extension $e_2$, and then to a third extension $e_3$ that has about 50 percent of the first extension $e_1$, followed by a further sudden reduction of the extension in z-direction to an extension $e_4$, which is about 10 percent of the first extension $e_1$ here. So, the enrichment zone 5 of the fluid channel 9 is divided into 4 different sections 18 here that each have a different extension $e_1$, $e_2$, $e_3$, $e_4$ in the z-direction.

Figure 8:
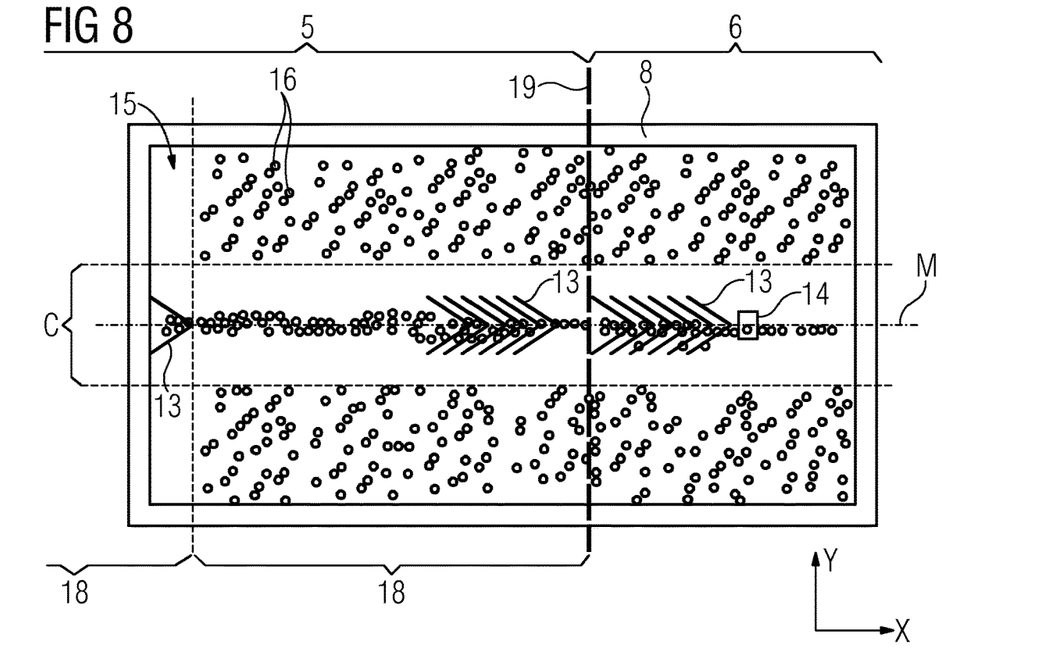
FIG. 8 shows an enlarged detail of the fluid channel of FIG. 7 in an x-y-plane.
Figure 9:
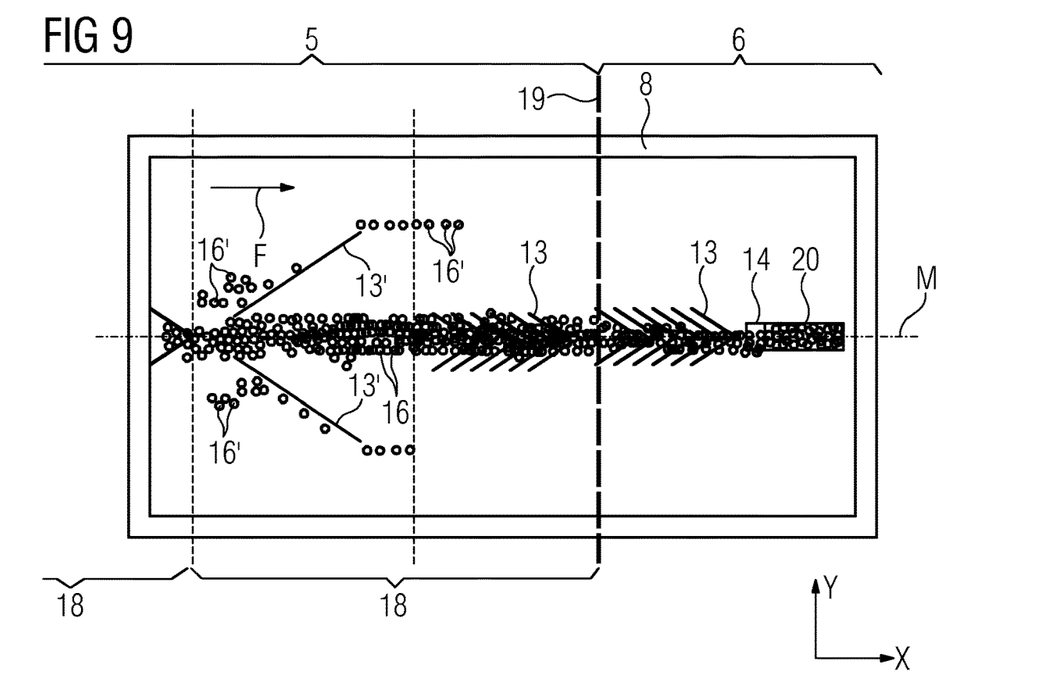
FIG. 9 shows a schematic illustration of an alternative embodiment of a fluid channel in detail, the detail corresponding to that shown in FIG. 8.

The decrease in extension $e_1$, $e_2$, $e_3$, $e_4$ in z-direction allows an adjustment of the shear rate of the particles 16 when they are flowing through the enrichment zone 5 of the fluid channel 9. The bottom of the fluid channel 9 may be closer to the magnet 8 in the measuring zone 6 than in the enrichment zone 5 for this purpose as well. On the bottom of the fluid channel 9, that is the surface of the fluid channel 9 that is closest to the magnet 8 beneath the cartridge 1, i.e. the enrichment zone 5 and the measuring zone 6 of the fluid channel 9, there are elevations 13 arranged in an x-y-plane perpendicular to the cross section shown here. Details of the elevations 13 are shown in FIGS. 7 to 9.

Figure 5:
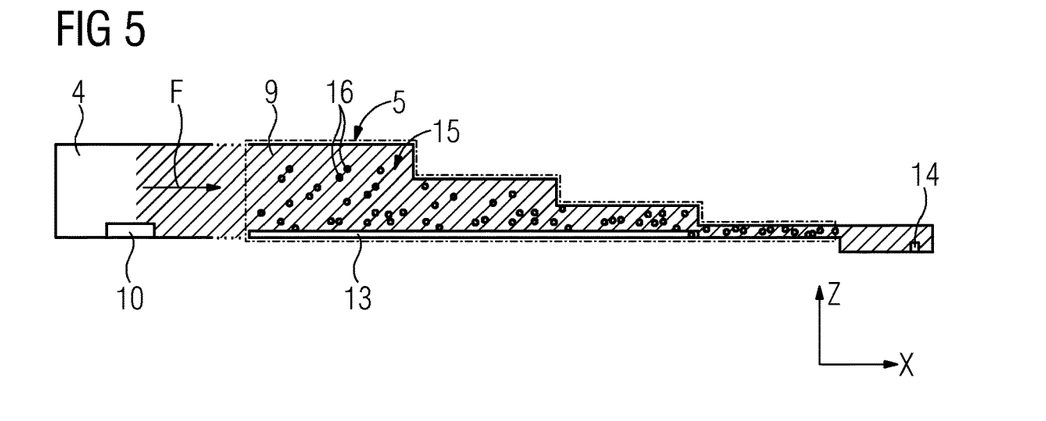
FIG. 5 shows the cross section of FIG. 4 with sample and particles in the fluid channel, without a magnet.

FIG. 5 shows the cross section of FIG. 4 with the sample 15 and the particles 16 in the enrichment zone 5 of the fluid channel 9. Here, the magnet 8 is removed, so no magnetic force is exerted on the particles 16 or their respective markers. Consequently, they are equally distributed in the z-direction in the enrichment zone 5.

Figure 6:
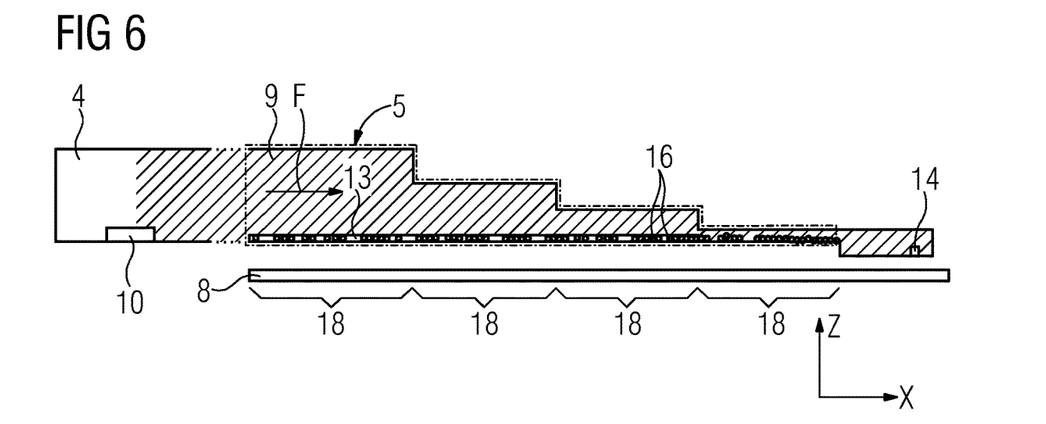
FIG. 6 shows the cross section of FIG. 4 with magnet and sample with particles in the fluid channel.

FIG. 6 shows the cross section of FIG. 5 with the magnet 8 in place. Due to the magnetic force exerted on the marked particles 16 by the magnet 8, all the marked particles are located on the bottom of the fluid channel 9 in the enrichment area 5. Consequently, the elevations 13 on the bottom of the fluid channel 9 may focus the marked particles 16 in a predetermined subsection of the fluid channel, for example the middle of a flow through the fluid channel 9 in an x-y-plane.

Figure 7:
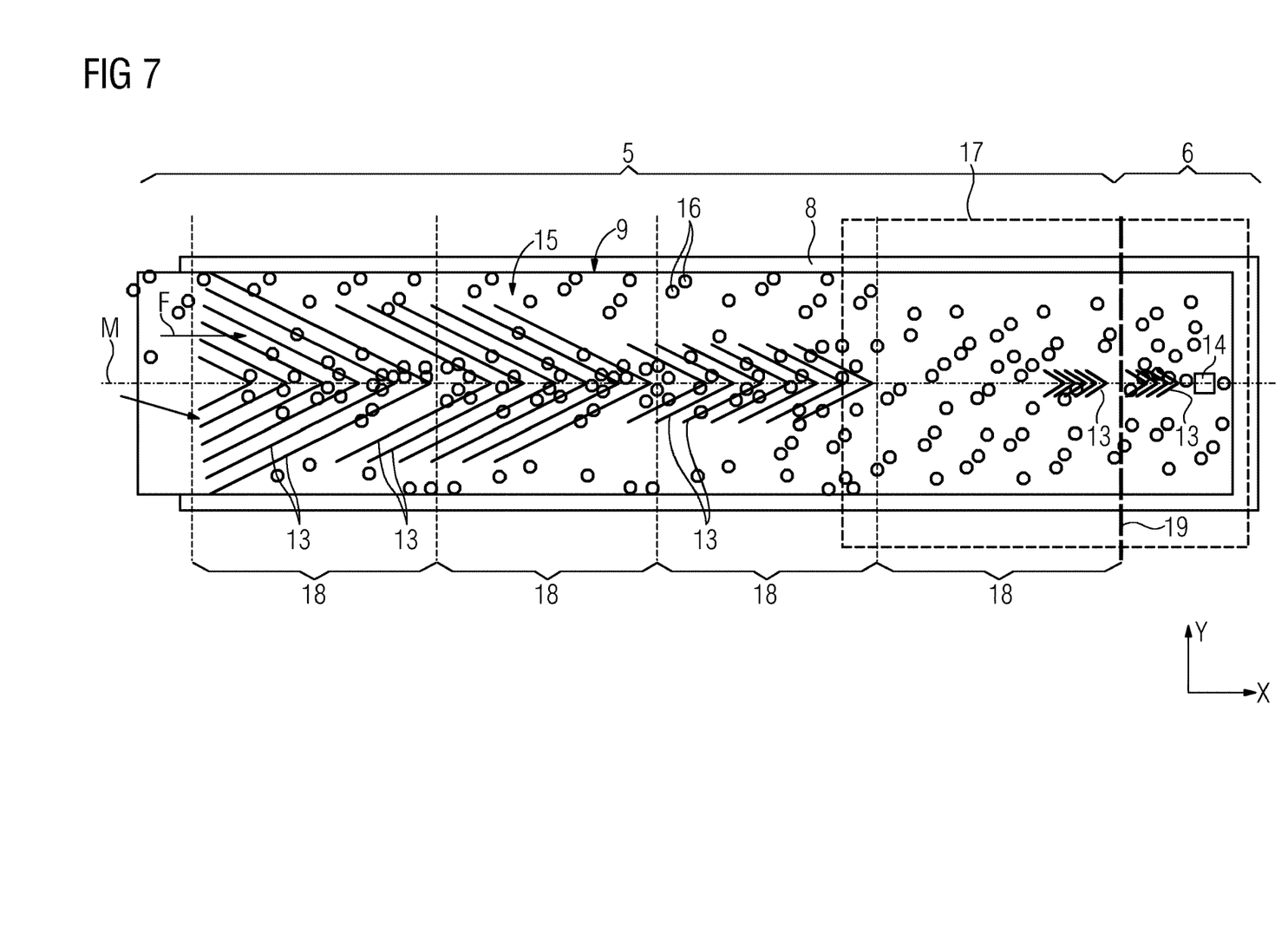
FIG. 7 shows a schematic illustration of an exemplary embodiment of a fluid channel in an enrichment zone and in a measuring zone in an x-y-plane.

FIG. 7 shows a schematic illustration of an exemplary embodiment of a fluid channel in an x-y-plane. Similar to FIGS. 4 to 6 there are four sections 14 of the fluid channel 9 that have a different extension in the z-direction. The fluid channel 9 is straight in the current example and features both an enrichment zone 5 and a measuring zone 6 that are separated by the line 19 for illustration purposes here. The fluid channel 9 has a flow direction F in which the sample 15 with the marked particles 16 is flowing. The enrichment zone 5 features again four different sections 18, each with a different extension in the z-direction in order to expose the particles 16 to a predefined shear rate. A box 17 marks a part of the fluid channel 9, the measuring zone 6 and a part of the enrichment zone 5 that will be shown in detail in FIG. 8.

On the bottom of the fluid channel 9 there are elevations 13 that drive or focus the marked particles 16 that are pulled to the bottom, in the present example by the magnet 8, to or in the middle M of the fluid channel 9 here. These elevations 13 are V-shaped in the present example with the tips of the v's being aligned in the middle M of the fluid channel 9 and pointing in the flow direction F. In the present example, there are several groups of elevations 13 that have the same dimensions. This means that the elevations 13 of some groups of elevations 13 extend in a direction perpendicular to the flow direction F less than the elevations 13 of other groups of elevations 13. Here, the elevations 13 extend less in that direction when they are closer to the measuring zone 6. Although the distance between the neighbouring elevations 13 may vary, in particular they may become closer to each other as they are closer to the measuring zone 6. So, from the perspective of a particle 16 flowing through the fluid channel 9 in the flow direction F the elevations 13 point towards the predetermined subsection of the fluid channel 9, which is the middle M of the fluid channel 9 in the present example. This is reasonable since the magnetic field sensor 14 is located exactly in the predetermined subsection of the fluid channel 9, that is, in the middle M of the fluid channel 9 in the flow-direction F.

The combination of a variation of the extension of the fluid channel 9 in the z-direction and the broadness of the elevations 13 allows to measure particles 16 in a large variety of different concentrations with the same cartridge 1. If the sample is a sample of whole blood, a dynamic range of more than two orders of magnitude, typically three to four orders of magnitude, can be covered for the concentrations of the predetermined particles 16 in the whole blood.

FIG. 8 shows an enlarged detail of the fluid channel of FIG. 7 that is marked by the box 17 in FIG. 7. The particles 16 around the middle M of the fluid channel 9 get concentrated in or focussed to the middle M by means of the elevations 13. Consequently, there is an almost homogenous concentration of the marked particles 16 outside a centre area C around the middle M of the fluid channel 9. Outside the centre area C, the particles 16 are not focussed any more. In the centre area C, almost all of the particles 16 are exactly in the middle M of the fluid channel 9 and hence flow by or pass the magnetic field sensor 14 one by one. As there are no other marked particles 16 in the close vicinity of the magnetic field sensor 14, the measurement results are not influenced by close-by particles 16.

FIG. 9 shows a schematic illustration of an alternative embodiment of a fluid channel 9 in detail, the detail corresponding to the detail shown in FIG. 8. Here, additional elevations 13' move particles 16' that have not been focused properly in the middle of the fluid channel away from the middle M. So, the ill-focused particles 16' do not mess with the measurement of the well-focussed particles 16. The ill-focussed particles 16' may be marked accidentally, for instance if the markers bind to particles the are not supposed to bind to. In this case, these particles 16' will be marked by significantly less markers than the pregiven particles, hence be influenced less by the magnetic field and not be focussed properly. In this example, the additional elevations 13' are straight elevations, similar to a V with an open tip that is orientated opposite to the v-shaped original elevations 13, i.e. with the open tip pointing against the flow direction F.

In addition, there has been added a well 20, in this embodiment right behind the magnetic field centre 14 in the flow direction F. This well 20 acts as a trap for the marked and measured particles 16. So the marked and measured particles 16 can be extracted easily after the measurement. The well 20 can be a cavity in the measuring zone 6 that extents in the z-direction so that, for example, the rest of the sample, e.g. blood, can be washed away with a buffer solution and the highly concentrated, measured particles 16 can be extracted as a purified sample of the measured particles 16.

Figure 10:
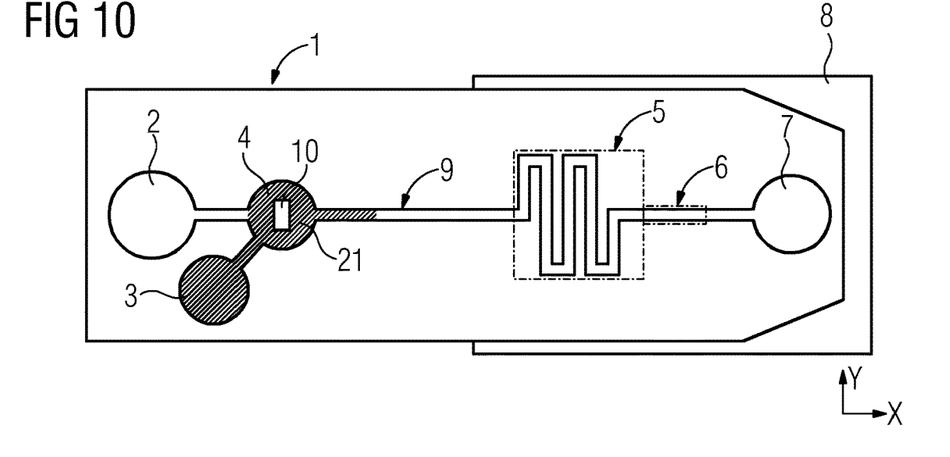
FIG. 10 shows a schematic illustration of the cartridge 1 of FIG. 1 with an activated blister in an x-y-plane.

FIG. 10 shows a schematic illustration of the cartridge 1 of FIG. 1 with an activated blister. Here, since the blister 3 has been activated and thus the buffer solution 21 and the markers previously contained in the blister 3 have been pushed into the fluid chamber 4, a part the buffer solution 21 has also been pushed into the fluid channel 9 connecting the fluid chamber 4 with the waste container 7 via the enrichment zone 5 and the measuring zone 6. The magnetic markers, however, will stay in the fluid chamber 4 due to the additional magnet 11 shown in FIG. 2. The buffer solution 21, however, will continue to flow through the fluid channel 9 when more of the buffer solution 21 with the markers or the sample 15 is pushed into the fluid chamber 4.

Figure 11:
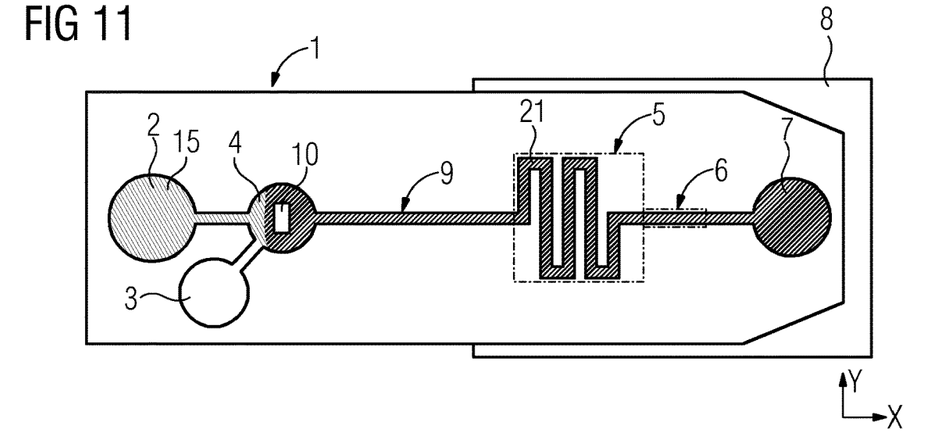
FIG. 11 shows the cartridge of FIG. 10 when a sample is injected into the cartridge.

FIG. 11 shows the cartridge of FIG. 10 with a sample injected into the inlet. Here, the sample 15 is already injected in the inlet 2 and has been partly flown into the fluid chamber 4. The sample 15 flowing into the fluid chamber 4 has pushed the buffer solution 21 further down the fluid channel 9 through enrichment zone 5 and measuring zone 6 towards the waste container 7. In the present example, the magnetic markers of the buffer solution 21 remained in the fluid chamber 4 because they have been fixed there by the additional magnet 11 (FIG. 1). The buffer solution 21 though has been flown through enrichment zone 5 and measuring zone 6 already. In a next step, either more of the sample 15 can be injected to the inlet 2 so that the rest of the buffer solution 21 is pushed out of the fluid chamber 4, or, as in the example shown in FIG. 12, the sample 15 can be mixed with the rest of the buffer solution 21 that remained in the fluid chamber 4 and with the magnetic markers. This results in a thinned sample 22 (FIG. 12) composed of the original sample 15 and the buffer solution 21, with marked particles 16 (FIG. 4-9) in the thinned sample 22 while the thinned sample 22 is still in the fluid chamber 4. This thinned sample 22 can then be pushed further through the fluid channel 9 towards the enrichment and measuring zone 6 by injecting more of the original sample 15 into the cartridge 1.

If the additional magnet remains activated at this point, the marked particles remain fixed in the fluid chamber 4 and are consequently surrounded by the original sample 15 in the following. This allows, after deactivating the additional magnet 11, measuring the marked particles as a part of the original sample 15, e.g. as a part of whole blood, hence mimicking in-vivo conditions in this example. If the additional magnet is deactivated prior to injecting more of the original sample 15 into the cartridge 1, the marked particles will be measured as a part of the thinned sample 22.

Figure 12:
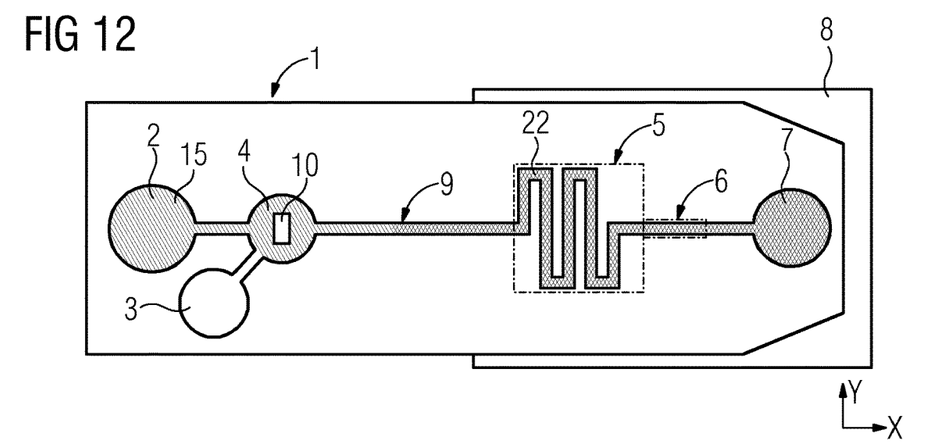
FIG. 12 shows the cartridge of FIG. 11 with the sample including marked particles flowing through an enrichment zone and a measuring zone into a waste container.

FIG. 12 shows the cartridge of FIG. 11 with the sample including marked particles flowing through an enrichment zone and a measuring zone into a waste container. Here, after the mixing of the sample 15 with magnetic markers and some of the buffer solution 21 remaining in the fluid chamber 4, the thinned sample 22 has been pushed further into the fluid channel 9 by injecting more of the original sample 15 into the cartridge 1. The additional magnet 11 has been switched off or moved away after the thinned sample 22 left the fluid chamber 4 to allow the marked particles 16 (FIGS. 4 to 9) that are now surrounded by the original sample 15, e.g. whole blood, to flow down the fluid channel 9. The thinned sample 22 is pushed through the enrichment zone 5 into the waste container 7 in the present example. When this process is complete, the original sample with the marked particles 16 (FIGS. 4 to 9) flows through the enrichment zone 5, where the said mechanical guiding structures, for example the elevations 13 (FIGS. 4 to 9), focus the marked particles 16 in a predetermined subsection of the fluid channel 9, for example the middle M of the fluid channel 9. So the marked particles 16 in the original sample 15 can be measured properly, for instance in in-vivo conditions, by a magnetic field sensor 14 (FIGS. 4 to 9). After flowing through the measuring zone 6, the original sample 15 including the marked particles 16 is pushed into the waste container 7 by a constant flow of original sample 15 in this example.

The invention claimed is:

1. A cartridge for a magnetic flow cytometer, extending in an x-y-plane, comprising:
    an inlet for injecting a sample into the cartridge,
    a blister for a buffer solution with magnetic markers to mark pregiven particles of the sample,
    an outlet, and
    a fluid channel, the fluid channel comprising a first part that connects the inlet with the blister and a second part that connects the first part with the outlet, wherein
        the second part of the fluid channel comprises:
            an enrichment zone with mechanical guiding structures to focus marked particles of the sample in a predetermined subsection of the fluid channel, and
            a measuring zone between the enrichment zone and the outlet, the measuring zone comprising a magnetic field sensor in the predetermined subsection of the fluid channel,
        wherein the mechanical guiding structures comprise a multitude of elevations extending on a surface of the fluid channel on the x-y-plane, and
        wherein the multitude of elevations each comprise a v-shape, wherein each v-shape is symmetrically connected in a tip;
    wherein each tip of each v-shaped elevation is longitudinally aligned along a middle of the fluid channel;
    a number of the mechanical guiding structures comprised in the fluid channel decrease in multitude as the fluid channel gets closer to the measuring zone.

2. The cartridge of claim 1, further comprising:
    a fluid chamber in the first part of the fluid channel, for mixing the sample with the markers.

3. The cartridge of claim 1, wherein:
    the mechanical guiding structures comprise the fluid channel decreasing stepwise in its extension in a z-direction in the enrichment zone as the fluid channel gets closer to the measuring zone.

4. The cartridge of claim 1, wherein:
    the multitude of elevations have an extension in a z-direction of more than half of a diameter of the particles that are to be marked.

5. The cartridge of claim 4, wherein:
    the multitude of elevations point, from a perspective of a flow through the fluid channel towards the outlet, either towards the predetermined subsection of the fluid channel to guide particles to the predetermined subsection or away from the predetermined subsection in order to guide away from the magnetic field sensor particles that are close to, but not within the predetermined subsection, or by combinations of elevations pointing towards and away from the predetermined subsection.

6. The cartridge of claim 5, wherein:
    the predetermined subsection of the fluid channel is the middle of the fluid channel on the surface in the x-y-plane of the fluid channel.

7. The cartridge of claim 5, wherein:
    the measuring zone comprises a well that, from the perspective of the flow through the fluid channel towards the outlet, is located behind the magnetic field sensor.

8. The cartridge of claim 4, wherein the multitude of elevations are walls.

9. The cartridge of claim 1,
wherein the fluid channel includes a plurality of turns in the enrichment zone in order to lengthen a path in which the particles are guided by the mechanical guiding structures.

10. The cartridge of claim 9, wherein the fluid channel in the enrichment zone includes the plurality of turns such that the fluid channel in the enrichment zone extends in an x direction, a positive y direction, and a negative y direction.

11. The cartridge of claim 1, wherein:
the fluid channel in the measurement zone has a broadness between 250 and 2500 μm and a height between 50 and 600 μm.

12. The cartridge of claim 1, further comprising a magnet positioned under the enrichment zone in a z direction.

13. The cartridge of claim 1, wherein the fluid channel has a first side and a second side, wherein the sample is configured to flow in the fluid channel between the first side and the second side, and wherein the multitude of elevations extend on a surface of the fluid channel between the first side and the second side.

\* \* \* \* \*